United States Patent [19]

Crouch

[11] Patent Number: 4,543,101

[45] Date of Patent: Sep. 24, 1985

[54] VALVE DEVICE TO AID IN RECONSTITUTING INJECTABLE POWDERS

[75] Inventor: Robert C. Crouch, Wilmington, Del.

[73] Assignee: Adria Laboratories, Inc., Columbus, Ohio

[21] Appl. No.: 594,057

[22] Filed: Mar. 28, 1984

[51] Int. Cl.⁴ ........ A61M 5/16

[52] U.S. Cl. ........ 604/411; 604/86

[58] Field of Search ........ 604/403–407, 604/411, 414, 415, 416, 86

[56] References Cited

U.S. PATENT DOCUMENTS

| | | | |
|---|---|---|---|
| 2,541,272 | 2/1951 | Murphy | 604/411 |
| 2,851,201 | 9/1958 | Poitras et al. | 604/411 |
| 3,603,471 | 9/1971 | Harris, Sr. et al. | 604/415 |
| 3,608,550 | 9/1971 | Stawski | 604/414 |
| 3,797,521 | 3/1974 | King | 604/405 |

FOREIGN PATENT DOCUMENTS

| | | | |
|---|---|---|---|
| 02506 | 11/1980 | European Pat. Off. | 604/415 |

*Primary Examiner*—John D. Yasko

*Attorney, Agent, or Firm*—Marion C. Staves

[57] ABSTRACT

A device for use in equalizing the pressure inside a vial during the addition or removal of fluid comprising a one piece sterilizable device for use in equalizing the pressure inside a vial during the addition or removal of fluid which comprises a cannula having a sharpened beveled lower end for puncturing the septum of a vial, a blunt upper end covered with a septum that can be punctured by the needle of a hypodermic syringe, and an enlarged annular portion below the blunt upper end limiting entry of the device into the vial, said enlarged annular portion having an air channel leading from the inside of the cannula through the enlarged annular portion to the outside of the cannula said air channel being provided at its outer end with means for one-way air flow.

1 Claim, 3 Drawing Figures

VALVE DEVICE TO AID IN RECONSTITUTING INJECTABLE POWDERS

FIELD OF THE INVENTION

This invention relates to a one piece device for use in reconstituting an injectable medicament. More particularly, this invention relates to a one piece device for equalizing the pressure inside a vial during the addition or removal of fluid.

BACKGROUND OF THE INVENTION

Many drugs are supplied in rubber stoppered vials in the form of dry powders or concentrates which have to be dissolved (reconstituted) or diluted with a fluid before use. In the past, the material in such vials has been reconstituted by inserting a conventional hypodermic needle through the rubber stopper and adding fluid. However, as this fluid fills the vial, air within the vial is compressed causing a pressure buildup. This may cause several problems. For example, when the needle used to add the fluid is withdrawn, small drops of the reconstituted solution may escape. If the reconstituted solution is one which may cause allergies or local skin reactions, the escape of only a few drops onto the doctor's or nurses hand may be undesirable. Also, in withdrawing samples from the vial, care must be taken that the pressure does not force the plunger of a unit dose syringe rearward so as to cause an overdose in the syringe.

OBJECTS AND SUMMARY OF THE INVENTION

An object of this invention is to provide a one piece, easy to handle, sterilizable device which allows easy addition or removal of fluid from a rubber stoppered vial at ambient pressure to avoid the possibility of accidents due to pressure differentials. This object and others have been met by the device of this invention.

The device of this invention comprises a cannula having a sharpened beveled lower end for puncturing the septum of a vial, a blunt upper end covered with a septum that can be punctured by the needle of a hypodermic syringe, and an enlarged annular portion below the upper end limiting entry of the device into the vial, said enlarged annular portion having an air channel leading from the inside of the cannula through the enlarged annular portion to the outside of the cannula, said air channel being provided at its outer end with means for one-way air flow.

DETAILED DESCRIPTION OF THE DRAWINGS

Figure 1:
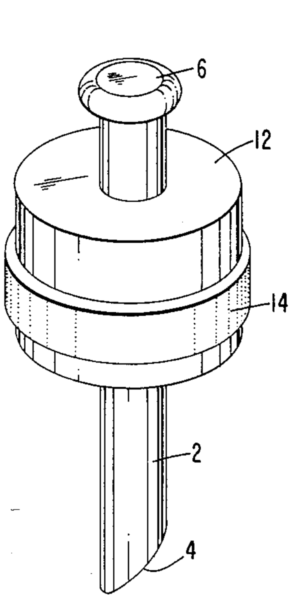
FIG. 1 is a perspective of one modification of the device of this invention.

FIG. 1 shows, in perspective view, a cannula (2) having a sharpened beveled lower end (4) and a blunt upper end (5) (not shown in this drawing) covered with a septum (6), and an enlarged annular portion (12) below the blunt upper end (5), having stretched around its circumference a rubber band (14) which acts as a means to control air flow.

Figure 2:
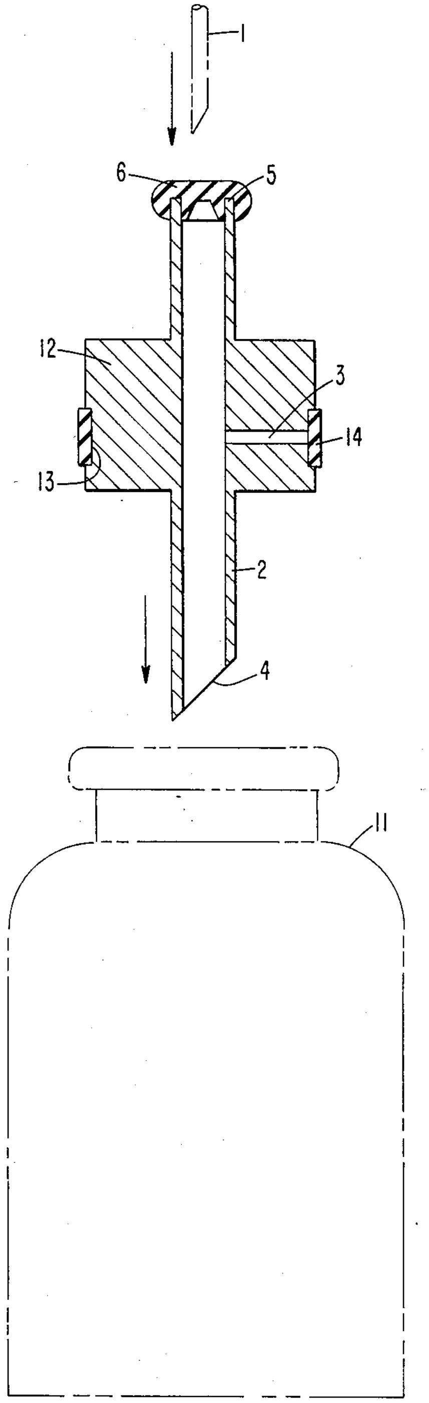
FIG. 2 is an elevation in cross-section of the modification of FIG. 1 in the closed position, along with the bottom of a hypodermic needle and the top half of a vial in phantom.

FIG. 2 shows a cross-sectional view along the longitudinal axis of the device of FIG. 1, having a cannula (2) with a sharpened and beveled lower end (4), a blunt upper end (5) covered with a septum (6) and an enlarged annular portion (12) below the blunt upper end (5), which limits entry into the vial (11), said enlarged annular portion (12) is shown with an air channel (3) leading from the inside of the cannula (2) through the enlarged annular portion (12) to the outside of the cannula (2) and covered at its outer end with a rubber band (14) which is stretched around the circumference of the enlarged annular portion (12) in a slot (13). Also shown, in phantom, is a hypodermic needle (1) ready to be inserted through the septum (6) into the cannula (2) and a vial (11) into which the device may be inserted.

Figure 3:
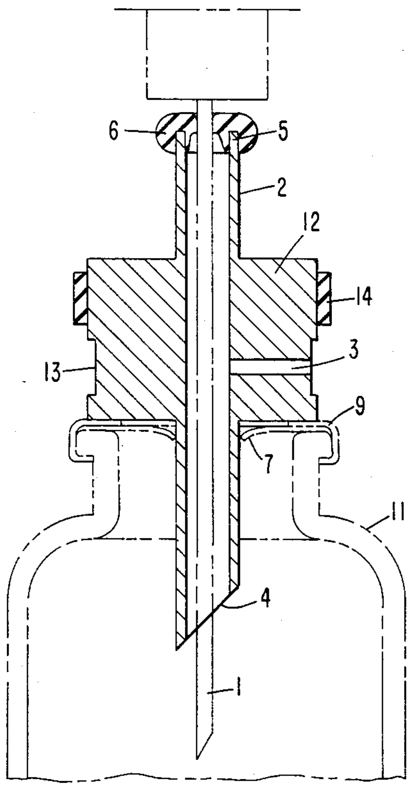
FIG. 3 is an elevation in cross-section of the modification of FIG. 1 in the open position showing the device inserted in a vial, shown in phantom, and with a hypodermic needle inserted in the device.

FIG. 3 shows a cross-section of the device of FIG. 1 taken along its longitudinal axis, having a cannula (2) with a sharpened and beveled lower end (4) piercing the rubber seal (7) on the top of the vial (11), a blunt upper end (5) covered with a septum (6), an enlarged annular portion (12) below the blunt upper end (5) which limits entry into the vial (11), said enlarged annular portion (12) is shown with an air channel (3) leading from the inside of the cannula (2) through the enlarged annular portion (12) to the outside of the cannula (2) and open at its outer end since the rubber band (14) which is stretched around the circumference of the enlarged annular portion (12) has been slipped out of its slot (13) and slid upward. Also shown in phantom is a hypodermic needle (1) piercing the septum (6) covering the upper end of the cannula (2) running through the cannula (2) and into the vial (11). The enlarged annular portion (12) is shown resting on the overseal (9) on the top of the vial (11).

The device of this invention can be manufactured from a number of various materials as will be obvious to those skilled in the art. For example, the device can be manufactured from any material which can be sharpened (at the beveled end) and sterilized. Typical of such materials are various metals, plastics and glass. Most preferably, however, the device will be manufactured from a metal such as stainless steel or surgical steel. The septum, at the end of the cannula, can be of any soft plastic or rubber. Most preferably, the septum will be easily replaceable.

The means for one-way air flow, located at the outer end of the air channel, can be as simple as a rubber band or if desired, a more complicated valve. The rubber band or valve will generally be made of some elastomeric material such as rubber or an elastomeric polymer.

The size of the device can vary. The optimum sizes will be obvious to those skilled in the art, since, for example, the diameter of the inside of the cannula must be sufficiently large to permit the insertion of a normal size hypodermic needle, yet small enough to easily insert through the rubber seal on a normal size vial. Likewise, the length of the cannula must be shorter than the length of the normal hypodermic needle.

In normal operation, the sharpened and beveled end of the cannula is inserted through the rubber septum covering the top of a vial. During this operation, the air channel is kept closed to maintain sterility. When using the device of FIG.'s 1, 2 and 3, this is accomplished by keeping the rubber band over the air channel. To fill the vial with fluid, one inserts the needle of a hypodermic filled with the fluid through the septum covering the upper end of the cannula. As the pressure in the vial increases, it forces the rubber band covering the air channel outward allowing sufficient air to escape to equalize the pressure, at which time the rubber band snaps back to cover the channel. When removing fluid from the vial, one inserts the needle of a hypodermic through the septum covering the upper end of the cannula and as one proceeds to empty the vial, lifts the rubber band covering the channel to allow air to enter, thus equalizing the pressure. The operation of other modifications of the device of this invention will be obvious to those skilled in the art.

What I claim and desire to protect by Letters Patent is:

1. A one-piece sterilizable device for use in equalizing the pressure inside a vial during the addition or removal of fluid which compares a cannula having a sharpened beveled lower end for puncturing the septum of a vial, a blunt upper end covered with a septum that can be punctured by the needle of a hypodermic syringe, and an enlarged annular portion below the blunt upper end limiting entry of the device into the vial, said enlarged annular portion having an air channel leading from the inside of the cannula through the enlarged annular portion to the outside of the cannula said air channel being provided at its outer end with means for one-way airflow, said means for one-way airflow being a rubber band stretched around the circumference of the enlarged annular portion.

* * * * *